(12) United States Patent
Daniel et al.

(10) Patent No.: US 8,378,153 B2
(45) Date of Patent: Feb. 19, 2013

(54) PROCESS FOR THE PRODUCTION OF ALCOHOL FROM A CARBONACEOUS FEEDSTOCK

(75) Inventors: Berian John Daniel, Beverley (GB); Jon Michael Stewart Deeley, Brough (GB); Benjamin Patrick Gracey, Hull (GB); Cong Rong Li, Hull (GB)

(73) Assignee: BP P.L.C., London (GB)

( * ) Notice: Subject to any disclaimer, the term of this patent is extended or adjusted under 35 U.S.C. 154(b) by 333 days.

(21) Appl. No.: 12/734,629

(22) PCT Filed: Nov. 7, 2008

(86) PCT No.: PCT/GB2008/003759
§ 371 (c)(1),
(2), (4) Date: Sep. 17, 2010

(87) PCT Pub. No.: WO2009/063173
PCT Pub. Date: May 22, 2009

(65) Prior Publication Data
US 2011/0004034 A1 Jan. 6, 2011

(30) Foreign Application Priority Data
Nov. 14, 2007 (EP) .................................. 07254448

(51) Int. Cl.
*C07C 27/04* (2006.01)
(52) U.S. Cl. ....................................................... 568/864
(58) Field of Classification Search ................... 568/864
See application file for complete search history.

(56) References Cited

FOREIGN PATENT DOCUMENTS

| DE | 32 21 077 | 12/1983 |
| EP | 0 030 110 A1 * | 6/1981 |
| EP | 0 167 300 | 1/1986 |
| EP | 2 186 787 A1 * | 5/2010 |
| GB | 385625 | 1/1933 |
| WO | WO 83/03409 | 10/1983 |

OTHER PUBLICATIONS

Written Opinion of the International Searching Authority for PCT/GB2008/003759, mailed Mar. 19, 2009.

* cited by examiner

*Primary Examiner* — Porfirio Nazario Gonzalez
(74) *Attorney, Agent, or Firm* — Nixon & Vanderhye

(57) ABSTRACT

The present invention relates to an improved process for the production of ethanol from a carbonaceous feedstock; wherein the carbonaceous feedstock is first converted to synthesis gas which is then converted to ethanoic acid, which is then esterified and which is then hydrogenated to produce ethanol.

10 Claims, 3 Drawing Sheets

PROCESS FOR THE PRODUCTION OF ALCOHOL FROM A CARBONACEOUS FEEDSTOCK

Figure 1:
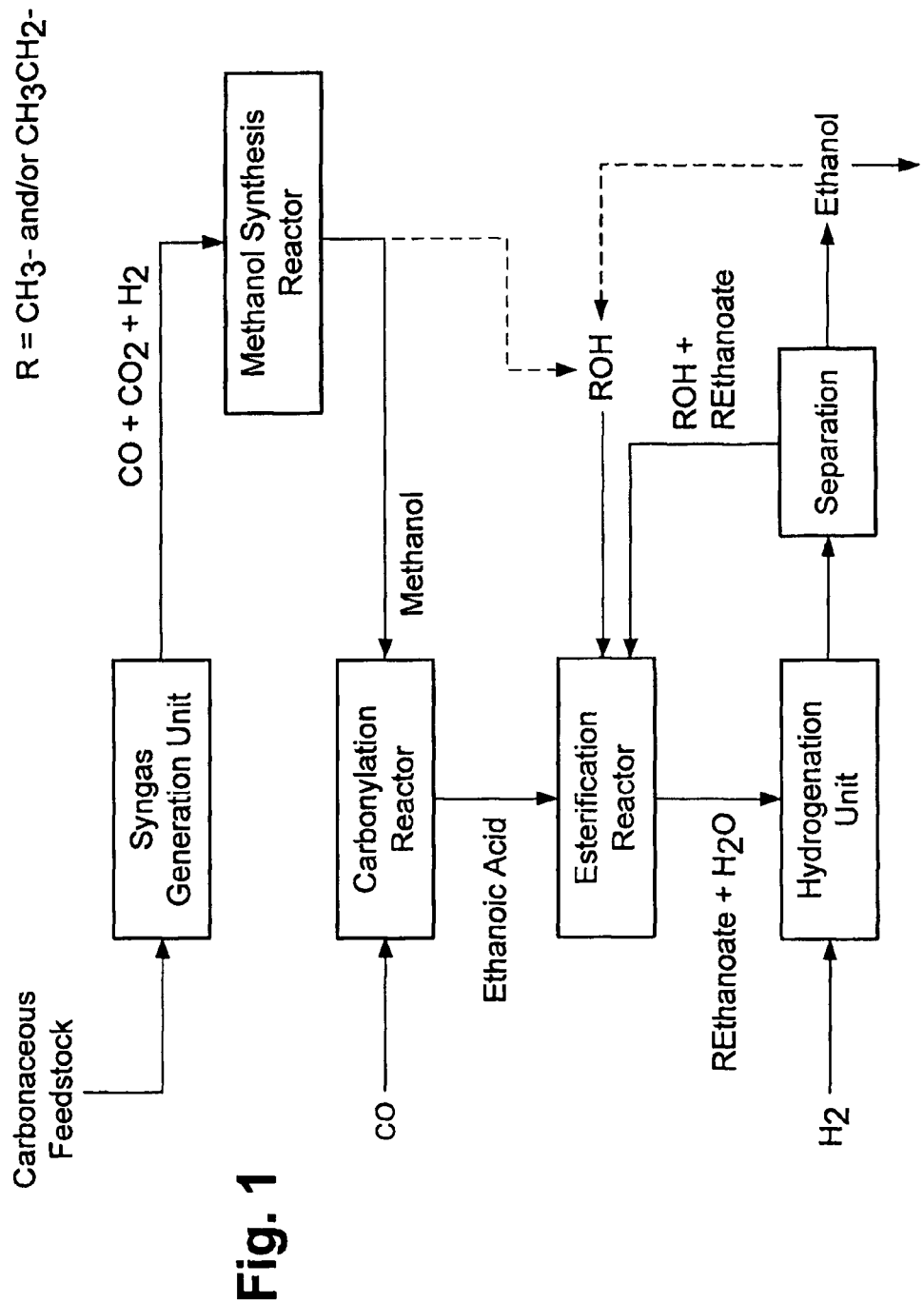

This application is the U.S. national phase of International Application No. PCT/GB2008/003759 filed 7 Nov. 2008, which designated the U.S. and claims priority to EP Application No. 07254448.9 filed 14 Nov. 2007, the entire contents of each of which are hereby incorporated by reference.

The present invention relates to an improved process for the production of ethanol from ethanoic acid.

In particular the present invention relates to an improved process for the production of ethanol from a carbonaceous feedstock; wherein the carbonaceous feedstock is first converted to synthesis gas which is then converted to ethanoic acid, which is then esterified and which is then hydrogenated to produce ethanol.

In recent years increased use and demand for alcohols such as methanol, ethanol and higher alcohols has led to a greater interest in processes relating to alcohol production. The said alcohols may be produced by the fermentation of, for example, sugars and/or cellulosic materials.

Alternatively alcohols, such as ethanol, may be produced from synthesis gas. Synthesis gas refers to a combination of $H_2$ and carbon oxides produced in a synthesis gas plant from a carbon source such as natural gas, petroleum liquids, biomass and other carbonaceous materials including coal, recycled plastics, municipal wastes, or any organic material. Thus, alcohol and alcohol derivatives may provide non-petroleum based routes for the production of valuable chemicals and fuels.

Generally, the production of alcohols, for example methanol, takes place via three process steps: synthesis gas preparation, methanol synthesis, and methanol purification. In the synthesis gas preparation step, an additional stage may be employed whereby the feedstock is treated, e.g. the feedstock is purified to remove sulphur and other potential catalyst poisons prior to being converted into synthesis gas. This treatment can also be conducted after synthesis gas preparation; for example, when coal or biomass is employed.

The reaction to produce alcohol(s) from synthesis gas is generally exothermic. The formation of $C_2$ and $C_{2+}$ alcohols is believed to proceed via the formation of methanol for modified methanol catalysts and cobalt molybdenum sulphide catalysts. However, the production of methanol is equilibrium-limited and thus requires high pressures in order to achieve viable yields. Hence, pressure can be used to increase the yield, as the reaction which produces methanol exhibits a decrease in volume, as disclosed in U.S. Pat. No. 3,326,956.

A low-pressure, copper-based methanol synthesis catalyst is commercially available from suppliers such as BASF, Johnson Matthey, and Haldor-Topsoe. Methanol yields from copper-based catalysts are generally over 99.5% of the converted $CO+CO_2$ present. Water is a by-product of the conversion of $CO_2$ to methanol and the conversion of CO synthesis gas to $C_2$ and $C_{2+}$ oxygenates. In the presence of an active water-gas shift catalyst, such as a methanol catalyst or a cobalt molybdenum catalyst the water equilibrates with the CO to give $CO_2$ and $H_2$. A paper entitled, "Selection of Technology for Large Methanol Plants," by Helge Holm-Larsen, presented at the 1994 World Methanol Conference, Nov. 30-Dec. 1, 1994, in Geneva, Switzerland, reviews the developments in methanol production and shows how further reduction in costs of methanol production will result in the construction of very large plants with capacities approaching 10,000 t per day.

Other processes for the production of $C_2$ and $C_{2+}$ alcohol(s), include the processes described hereinafter;

WO 8303409 describes a process whereby ethanol is produced by carbonylation of methanol by reaction with CO in the presence of a carbonylation catalyst to form ethanoic acid which is then converted to an ethanoate ester followed by hydrogenolysis of the ethanoate ester formed to give ethanol or a mixture of ethanol and another alcohol which can be separated by distillation. Carbonylation can be effected using a $CO/H_2$ mixture and hydrogenolysis can similarly be conducted in the presence of CO, leading to the possibility of circulating gas between the carbonylation and hydrogenolysis zones with synthesis gas, preferably a 2:1 $H_2$:CO molar mixture being used as make up gas.

U.S. Pat. No. 4,122,110 relates to a process for manufacturing alcohols, particularly linear saturated primary alcohols, by reacting CO with $H_2$ at a pressure between 2 and 25 MPa and a temperature between 150 and 400° C., in the presence of a catalyst, characterized in that the catalyst contains at least 4 essential elements: (a) copper (b) cobalt (c) at least one element M selected from chromium, iron, vanadium and manganese, and (d) at least one alkali metal.

U.S. Pat. No. 4,831,060 relates to the production of mixed alcohols from CO and $H_2$ gases using a catalyst, with optionally a co-catalyst, wherein the catalyst metals are molybdenum, tungsten or rhenium, and the co-catalyst metals are cobalt, nickel or iron. The catalyst is promoted with a Fischer-Tropsch promoter like an alkali or alkaline earth series metal or a smaller amount of thorium and is further treated by sulphiding. The composition of the mixed alcohols fraction can be selected by selecting the extent of intimate contact among the catalytic components.

Journal of Catalysis, 1988, 114, 90-99 discloses a mechanism of ethanol formation from synthesis gas over $CuO/ZnO/Al_2O_3$. The formation of ethanol from CO and $H_2$ over a CuO/ZnO methanol catalyst is studied in a fixed-bed microreactor by measuring the isotopic distribution of the carbon in the product ethanol when isotopically-enriched $^{13}C$ methanol was added to the feed.

As the importance of ethanol is ever increasing in today's world, so is the need and desire to produce ethanol from a carbonaceous feedstock with a higher carbon efficiency, a higher conversion and an improved productivity and selectivity. Hence, the present invention provides a process that allows one to produce ethanol from a carbonaceous feedstock, with an improved carbon efficiency, a higher selectivity and, in particular, with a more productive conversion to ethanol; this is achieved primarily by operating under optimized water conditions within the hydrogenation reactor.

Figure 2:
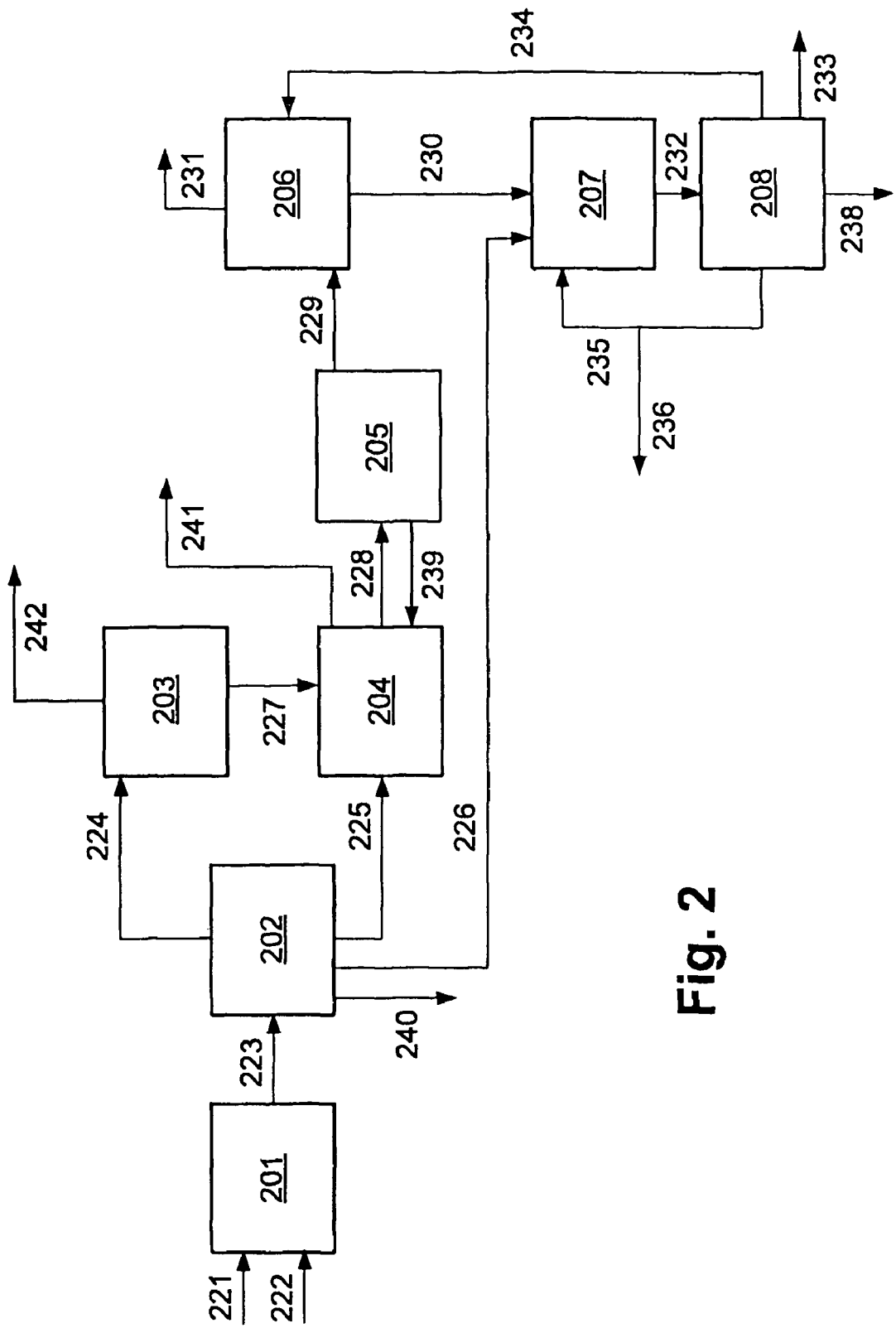
Figure 3:
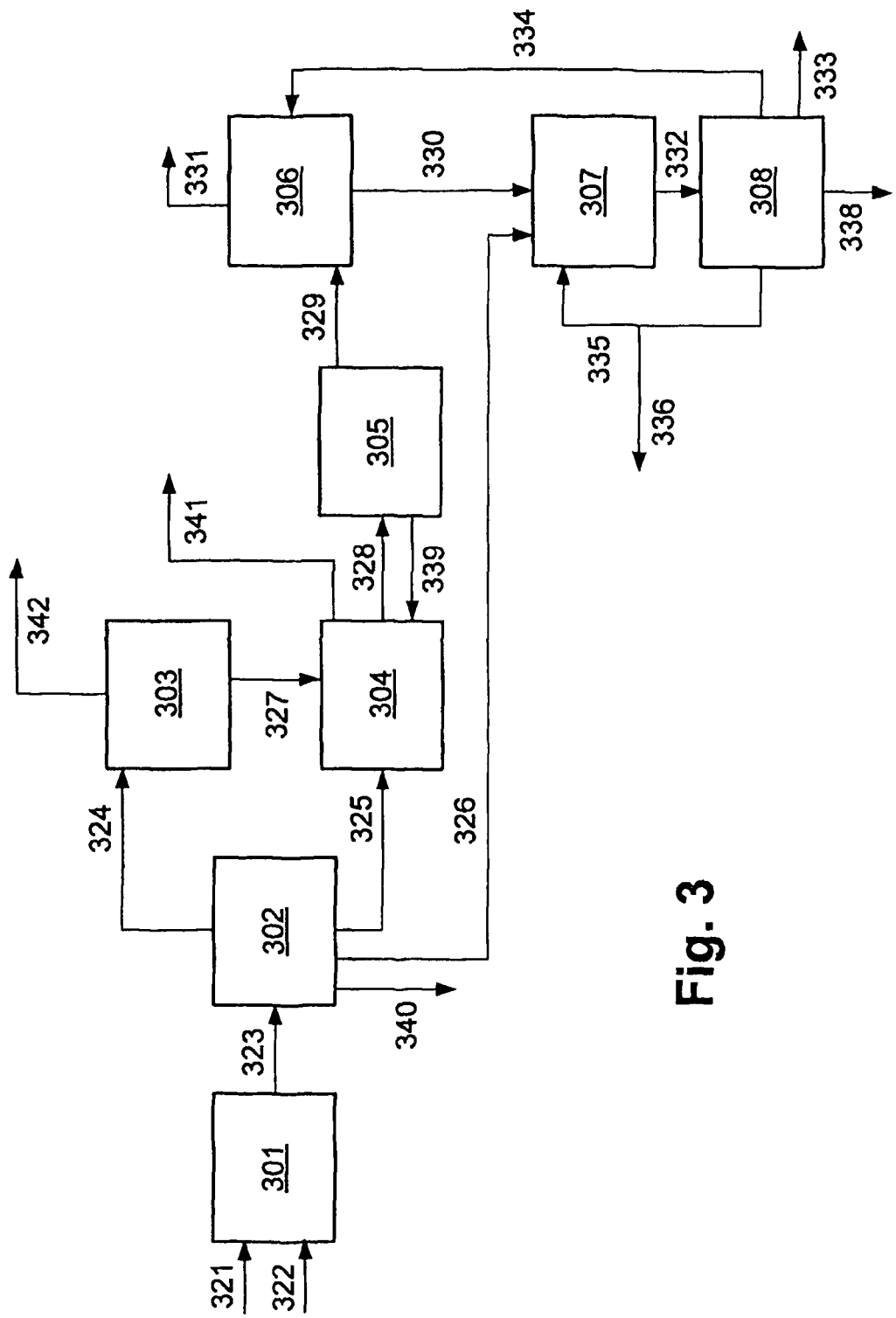

FIGS. 1, 2 and 3 represent embodiments of a process scheme according to the present invention wherein the references correspond to those used in the present description and appending claims.

Thus, the present invention relates to an improved process for the production of ethanol from ethanoic acid and $H_2$, characterised by the following steps:

1) introducing ethanoic acid, together with methanol and/or ethanol into an esterification reactor to produce methyl ethanoate and/or ethyl ethanoate (hereinafter referred individually or collectively as "ethanoate"),
2) introducing ethanoate from step 1, together with $H_2$ and water, into a hydrogenation unit to produce a stream comprising ethanol, unreacted ethanoate and optionally methanol,
3) separating the resulting stream, from step 2, into unreacted ethanoate and ethanol and optionally methanol, 4) optionally reintroducing ethanoate, from step 3, into the esterification reactor of step 1,
5) using at least a part of the methanol and/or the ethanol of step 3, as the methanol and/or ethanol feed of the esterification reactor of step 1, and
6) recovering ethanol, from step 3.

The present invention also relates to an improved process for the production of ethanol from methanol, characterised by the following steps:
1) introducing methanol, together with CO, into a carbonylation reactor, to produce ethanoic acid,
2) introducing ethanoic acid from step 1, together with methanol and/or ethanol, into an esterification reactor to produce methyl ethanoate and/or ethyl ethanoate (hereinafter referred individually or collectively as "ethanoate"),
3) introducing at least a part of the ethanoate from step 2, together with $H_2$ and water, into a hydrogenation unit to produce a stream comprising ethanol, unreacted ethanoate and optionally methanol,
4) separating the resulting stream, from step 3, into unreacted ethanoate and ethanol and optionally methanol,
5) optionally reintroducing ethanoate, from step 4, into the esterification reactor of step 2,
6) using at least a part of the methanol and/or the ethanol of step 4, as the methanol and/or ethanol feed of the esterification reactor of step 2, and
7) recovering ethanol, from step 4.

Furthermore, the present invention also relates to an improved process for the production of ethanol from a carbonaceous feedstock, whereby a carbonaceous feedstock is first converted into synthesis gas, which is subsequently converted into ethanol, characterised by the following consecutive steps:
1) introducing a carbonaceous feedstock, into a synthesis gas generation unit to produce synthesis gas,
2) introducing synthesis gas, produced in step 1, into a methanol synthesis reactor to produce methanol,
3) introducing methanol from step 2, together with CO, into a carbonylation reactor, to produce ethanoic acid,
4) introducing ethanoic acid from step 3, together with methanol and/or ethanol, into a esterification reactor to produce methyl ethanoate and/or ethyl ethanoate (hereinafter referred individually or collectively as "ethanoate"),
5) introducing ethanoate from step 4, together with $H_2$ and water, into a hydrogenation unit to produce a stream comprising ethanol, unreacted ethanoate and optionally methanol,
6) separating the resulting stream, from step 5, into unreacted ethanoate and ethanol and optionally methanol,
7) optionally reintroducing ethanoate, from step 6, into the esterification reactor of step 4,
8) using at least a part of the methanol and/or the ethanol of step 6, as the methanol and/or ethanol feed of the esterification reactor of step 4, and
9) recovering ethanol, from step 6.

For the purposes of the present invention and appending claims the following terms are defined hereinafter:

The 'dew point temperature' is a threshold temperature, for example, for a given pure component or mixture of components, at a given pressure, if the system temperature is raised to above the dew point temperature, the mixture will exist as a dry gas. Likewise below the dew point temperature, the mixture will exist as a vapour containing some liquid.

'Gas' and/or 'gas phase' are defined as a pure component, or mixture of components, that are above the dew point temperature.

'Gas hourly space velocity' (GHSV) is defined as the volume of gas fed per unit volume of catalyst per hour, at standard temperature (0° C.) and pressure (0.101325 MPa).

'Liquid hourly space velocity' (LHSV) is defined as the volume of liquid fed per unit volume of catalyst per hour.

According to one aspect of the present invention, the synthesis gas feedstock, a mixture of carbon oxide(s) and $H_2$, that is used to produce the methanol feed stream, is preferably produced from a carbonaceous feedstock.

The carbonaceous feedstock is preferably a material such as biomass, plastic, naphtha, refinery bottoms, crude synthesis gas (from underground coal gasification or biomass gasification), smelter off gas, municipal waste, coal bed methane, coal, and/or natural gas, with coal and natural gas being the preferred sources. To one skilled in the art a combination of sources can also be used, for example coal and natural gas to advantageously increase the $H_2$ to carbon ratio.

Natural gas commonly contains a range of hydrocarbons (e.g. $C_1$-$C_3$ alkanes), in which methane predominates. In addition to this, natural gas will usually contain nitrogen, $CO_2$ and sulphur compounds. Preferably the nitrogen content of the feedstock is less than 40 mol %, more preferably less than 10 mol % and most preferably less than 2 mol %.

Processes for producing synthesis gas, in a synthesis gas plant, are well known. Each method has its advantages and disadvantages, and the choice of using a particular reforming process over another is governed by economic and available feed stream considerations, as well as by the desire to obtain the optimum ($H_2$—$CO_2$):(CO+$CO_2$) molar ratio in the resulting synthesis gas that is suitable for further chemical processing. A discussion of the available synthesis gas production technologies is provided in both Hydrocarbon Processing, 1999, 78:4, 87-90, and 92-93 and Petrole et Techniques, 1998, 415, 86-93, and are both hereby incorporated by reference.

It is also known that the synthesis gas may be obtained by catalytic partial oxidation of hydrocarbonaceous material in a microstructured reactor as exemplified in IMRET 3: Proceedings of the Third International Conference on Microreaction Technology, ed. W. Ehrfeld, Springer Verlag, 1999, pages 187-196. Alternatively, the synthesis gas may be obtained by short contact time catalytic partial oxidation of hydrocarbonaceous feedstocks as described in EP 0303438. The synthesis gas can also be obtained via a 'compact reformer' process as described in Hydrocarbon Engineering, 2000, 5:5, 67-69; Hydrocarbon Processing, 2000, 79:9, 34; Today's Refinery, 2000, 15:8, 9; WO 9902254; and WO 0023689.

Typically, for commercial synthesis gas production the pressure at which the synthesis gas is produced from a steam reformer ranges from approximately 0.1 to 10 MPa, preferably 2 to 3 MPa and the temperatures at which the synthesis gas exits the reformer ranges from approximately 700 to 1000° C. Likewise, for commercial synthesis gas production the pressure at which the synthesis gas is produced from an auto-thermal reformer ranges from approximately 0.1 to 10 MPa, preferably 2 to 5 MPa and the temperatures at which the synthesis gas exits the reformer ranges from approximately 700 to 1300° C. Where the high temperatures are necessary in order to produce a favourable equilibrium for synthesis gas production, and to avoid metallurgy problems associated with carbon dusting. The synthesis gas contains a molar ratio of ($H_2$—$CO_2$):(CO+$CO_2$) ranging from 0.8 to 3M, which is dependent on the carbonaceous feedstock(s) and the method of reforming used. For example, when natural gas is used as the carbonaceous feedstock for steam reforming, the synthesis gas obtained usually has a maximum $(H_2—CO_2):(CO+CO_2)$ ratio of 3.0. However, when natural gas is used as the carbonaceous feedstock for auto-thermal reforming, the synthesis gas obtained usually has a $(H_2—CO_2):(CO+CO_2)$ ratio of 1.5.

According to a preferred embodiment of the present invention, the molar ratio, $(H_2—CO_2):(CO+CO_2)$, of the synthesis gas stream exiting the synthesis gas generation unit(s) is greater than 1.6, more preferably greater than 1.8 and most preferably greater than 2.0. Preferably, the molar ratio, $(H_2—CO_2):(CO+CO_2)$, of said synthesis gas stream exiting the synthesis gas generation unit(s) is less than 3.0, preferably less than 2.75, more preferably less than 2.4 and most preferably less than 2.2.

According to another embodiment of this invention when the carbonaceous feedstock used for synthesis gas generation is not an aliphatic hydrocarbon (e.g. coal, aromatic material, biomass) the molar ratio $(H_2—CO_2):(CO+CO_2)$ of the exit synthesis gas is preferably adjusted to the target value by addition of $H_2$ or removal of $CO_2$.

According to a preferred embodiment of the present invention, the exit stream obtained from the synthesis gas reactor (e.g. using a steam reformer), comprises essentially a mixture of carbon oxide(s) and $H_2$. It can also comprise water, nitrogen and traces of unconverted hydrocarbons (e.g. $C_1$-$C_3$ alkanes).

According to a preferred embodiment of the present invention, during synthesis gas generation, an additional stage may be employed whereby the feedstock is first purified to remove sulphur and other potential catalyst poisons (such as halides or metals e.g. mercury) prior to being converted into synthesis gas; alternatively this treatment can also be performed after synthesis gas preparation for example, when coal or biomass are used.

According to an embodiment of the present invention, at least part of the said synthesis gas stream is then introduced into a methanol synthesis unit, in order to produce a stream comprising methanol. Preferably the molar ratio, $(H_2—CO_2):(CO+CO_2)$, of said synthesis gas feed stream fed into the methanol synthesis reactor is greater than 1.6, more preferably greater than 1.8 and most preferably greater than 2.0. Preferably the molar ratio, $(H_2—CO_2):(CO+CO_2)$, of said synthesis gas feed stream fed into the methanol synthesis reactor is less than 3.0, more preferably less than 2.5 and most preferably less than 2.2.

According to a preferred embodiment of the present invention, the methanol synthesis unit may be any reactor that is suitable for producing methanol, for example a fixed bed reactor, which can be run in adiabatic or isothermal mode e.g. a multi-tubular reactor; or a fluidised bed reactor.

Preferably the methanol synthesis unit is operated at a temperature of more than 200° C., preferably more than 220° C. and most preferably more than 240° C.; and less than 310° C., preferably less than 300° C. and most preferably less than 290° C. Preferably the methanol synthesis unit is operated at pressure of more than 2 MPa and preferably more than 5 MPa; and less than 10 MPa and preferably less than 9 MPa. In fact, since methanol synthesis is an exothermic reaction, the chosen temperature of operation is governed by a balance of promoting the forward reaction (i.e. by not adversely affecting the equilibrium) and aiding the rate of conversion (i.e. higher productivity).

The catalysts used for methanol synthesis can be divided into 2 groups:
i. the high pressure zinc catalysts, composed of zinc oxide and a promoter; and
ii. low pressure copper catalysts, composed of zinc oxide, copper oxide, and a promoter.

Hence, according to a preferred embodiment of the present invention, the preferred methanol synthesis catalyst is a mixture of copper, zinc oxide, and a promoter such as, chromia or alumina. Under the aforementioned operating conditions, these said mixtures can catalyse the production of methanol from CO and $H_2$ with a high selectivity.

Additionally by-products such as methane, ethanol and other higher alcohols may also be produced during methanol synthesis. According to a preferred embodiment of this aspect of the present invention, the stream exiting the methanol synthesis reactor is subsequently purified to remove said by-products by any methods known to those skilled in the art.

According to another aspect of the present invention, a methanol stream, together with a substantially pure CO stream, are introduced into a carbonylation reactor. Preferably, at least part of the said methanol stream emanates from the aforementioned methanol synthesis unit, however said methanol stream may also emanate from another suitable source, such as a bio-fermentation process and/or pyrolysis (e.g. wood pyrolysis).

Preferably at least a part of the said CO stream is obtained from the aforementioned synthesis gas generation stage. This is preferably performed by first removing $CO_2$ and water from the generated synthesis gas followed by a cryogenic separation to isolate the substantially pure CO from the $H_2$. Alternative methods of separation, such as membrane separation technologies can also be employed. Alternatively, said CO stream may also be obtained from another suitable source, such as another chemical process (e.g. off-gas from steel manufacture). Said CO stream(s) may still contain inert impurities such as $CO_2$, methane, nitrogen, noble gases, water and $C_1$ to $C_4$ paraffinic hydrocarbons, which are preferably removed before use.

According to this aspect of the present invention, the step of introducing methanol, together with CO, into a carbonylation reactor is performed under conditions favourable for producing ethanoic acid.

There are many examples in the prior art which disclose carbonylation processes that can be suitably used in the present invention.

For example, such carbonylation processes can be made in the presence of iridium catalysts as described in U.S. Pat. No. 3,772,380. UK patent GB 1276326 also describes the preparation of mono-carboxylic acids by carbonylation of alcohols in the presence of rhodium or iridium catalysts, halogen promoters and water or an alcohol, ether or ester.

Carbonylation processes in the presence of ruthenium and osmium catalysts can also be suitably used in the present invention. Thus, UK patents GB 1234641 and GB 1234642 describe a process for the production of an organic acid by carbonylation of an alcohol in the presence of a noble metal catalyst selected from iridium, platinum, palladium, osmium and ruthenium and their compounds and a promoter which is halogen or halogen compound. According to Jenner et al, Journal of Molecular Catalysis, 1987, 40, 71-82 ruthenium compounds are effective carbonylation catalysts for converting primary alcohols into acids at high CO pressures. Standard conditions of 45 MPa CO pressure were used in the reported experiments. For example, UK patent application GB 2029409 describes a process for the preparation of aliphatic carboxylic acids by reacting CO with alcohols at an elevated pressure of 3.4 MPa or greater in the presence of a ruthenium catalyst and halogen-containing promoter.

According to a preferred embodiment of this aspect of the present invention, the carbonylation process takes place in the presence of an iridium catalyst together with at least one promoter; indeed, such catalyst systems have proven to have beneficial effects on the rate of carbonylation of methanol. Said carbonylation process is thus preferably performed in the presence of at least a finite concentration of water with a catalyst system comprising:
(a) an iridium catalyst, (b) methyl iodide and (c) at least one promoter.

Thus, according to a preferred embodiment of this aspect of the present invention the process for the production of ethanoic acid by carbonylation of methanol comprises contacting methanol with CO, in the liquid reaction composition, in a carbonylation reactor wherein, the liquid reaction composition comprises:
(a) ethanoic acid, (b) an iridium catalyst, (c) methyl iodide, (d) water and (e) at least one promoter.

According to an embodiment of this aspect of the present invention, during the carbonylation process, water may be formed in situ in the liquid reaction composition. For example, water may be produced via by-product formation, generated during methane production. Water may also be generated during the esterification reaction between methanol reactant and ethanoic acid product. Water may also be introduced to the carbonylation reactor together with, or separately from, other components of the liquid reaction composition. Water may be separated from other components of reaction composition withdrawn from the reactor and may be recycled in controlled amounts to maintain a preferred concentration of water in the liquid reaction composition. Preferably, the concentration of water in the liquid reaction composition of the carbonylation reactor is in the range 0.1 to 15 wt %, more preferably 1 to 10 wt %, most preferably 1 to 6.5 wt %.

The iridium catalyst in the liquid reaction composition may comprise any iridium containing compound which is soluble in the liquid reaction composition. The iridium catalyst may be added to the liquid reaction composition for the carbonylation reaction in any suitable form which dissolves in the liquid reaction composition or is convertible to a soluble form. Examples of suitable iridium-containing compounds which may be added to the liquid reaction composition include $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_2I_2]^-H^+$, $[Ir(CO)_2Br_2]^-H^+$, $[Ir(CO)_2I_4]^-H^+$, $[Ir(CH_3)I_3(CO)_2]^-H^+$, $Ir_4(CO)_{12}$, $IrCl_3.3H_2O$, $IrBr_3.3H_2O$, $Ir_4(CO)_{12}$, iridium metal, $Ir_2O_3$, $IrO_2$; $Ir(acac)(CO)_2$, $Ir(acac)_3$, iridium ethanoate, $[Ir_3O(OAc)_6(H_2O)_3][OAc]$, and hexachloroiridic acid $[H_2IrCl_6]$, preferably, chloride-free complexes of iridium such as ethanoates, oxalates and acetoacetates which are soluble in one or more of the carbonylation reaction components such as water, alcohol and/or carboxylic acid. Particularly preferred is green iridium ethanoate which may be used in an ethanoic acid or aqueous ethanoic acid solution.

Preferably, the iridium carbonylation catalyst concentration in the liquid reaction composition is in the range 100 to 6000 ppm by weight of iridium, more preferably 700 to 3000 ppm by weight of iridium.

In the process of the present invention at least one promoter is present in the reaction composition. Suitable promoters are preferably selected from the group consisting of ruthenium, osmium, rhenium, cadmium, mercury, zinc, gallium, indium and tungsten, and are more preferably selected from ruthenium and osmium and most preferably is ruthenium. Preferably, the promoter is present in an effective amount up to the limit of its solubility in the liquid reaction composition and/or any liquid process streams recycled to the carbonylation reactor from the ethanoic acid recovery stage. The promoter is suitably present in the liquid reaction composition at a molar ratio of promoter:iridium of [0.5 to 15]:1. As noted above, the beneficial effect of a promoter such as ruthenium has been found to be greatest at the water concentration which gives the maximum carbonylation rate at any defined methyl ethanoate and methyl iodide concentration. A suitable promoter concentration is 400 to 5000 ppm by weight.

The promoter may comprise any suitable promoter metal-containing compound which is soluble in the liquid reaction composition. The promoter may be added to the liquid reaction composition for the carbonylation reaction in any suitable form which dissolves in the liquid reaction composition or is convertible to soluble form.

Examples of suitable ruthenium-containing compounds which may be used as sources of promoter include ruthenium (III) chloride, ruthenium (III) chloride trihydrate, ruthenium (IV) chloride, ruthenium (III) bromide, ruthenium metal, ruthenium oxides, ruthenium (III) methanoate, $[Ru(CO)_3I_3]^-H^+$, $[Ru(CO)_2I_2]_n$, $[Ru(CO)_4I_2]$, $[Ru(CO)_3I_2]_2$, tetra(aceto) chlororuthenium(II,III), ruthenium (III) ethanoate, ruthenium (III) propanoate, ruthenium (III) butanoate, ruthenium pentacarbonyl, triruthenium dodecacarbonyl and mixed ruthenium halocarbonyls such as dichlorotricarbonylruthenium (II) dimer, dibromotricarbonylruthenium (II) dimer, and other organoruthenium complexes such as tetrachlorobis (4-cymene)diruthenium(II), tetrachlorobis(benzene)diruthenium(II), dichloro(cycloocta-1,5-diene)ruthenium (II) polymer and tris(acetylacetonate)ruthenium (III).

Examples of suitable osmium-containing compounds which may be used as sources of promoter include osmium (III) chloride hydrate and anhydrous, osmium metal, osmium tetraoxide, triosmiumdodecacarbonyl; $[O_s(CO)_4I_2]$, $[Os(CO)_3I_2]_2$, $[Os(CO)_3I_3]^-H^+$, pentachloro-mu-nitrodiosmium and mixed osmium halocarbonyls such as tricarbonyldichloroosmium (II) dimer and other organoosmium complexes.

Examples of suitable rhenium-containing compounds which may be used as sources of promoter include $Re_2(CO)_{10}$, $Re(CO)_5Cl$, $Re(CO)_5Br$, $Re(CO)_5I$, $ReCl_3.xH_2O$, $[Re(CO)_4I]_2$, $[Re(CO)_4I_2]^-H^+$, and $ReCl_5.yH_2O$.

Examples of suitable cadmium-containing compounds which may be used include $Cd(OAc)_2$, $CdI_2$, $CdBr_2$, $CdCl_2$, $Cd(OH)_2$, and cadmium acetylacetonate.

Examples of suitable mercury-containing compounds which may be used as sources of promoter include $Hg(OAc)_2$, $HgI_2$, $HgBr_2$, $HgCl_2$, $Hg_2I_2$, and $Hg_2Cl_2$.

Examples of suitable zinc-containing compounds which may be used as sources of promoter include $Zn(OAc)_2$, $Zn(OH)_2$, $ZnI_2$, $ZnBr_2$, $ZnCl_2$, and zinc acetylacetonate. Examples of suitable gallium-containing compounds which may be used as sources of promoter include gallium acetylacetonate, gallium ethanoate, $GaCl_3$, $GaBr_3$, $GaI_3$, $Ga_2Cl_4$ and $Ga(OH)_3$.

Examples of suitable indium-containing compounds which may be used as sources of promoter include indium acetylacetonate, indium ethanoate, $InCl_3$, $InBr_3$, $InI_3$, $InI$ and $In(OH)_3$.

Examples of suitable tungsten-containing compounds which may be used as sources of promoter include $W(CO)_6$, $WCl_4$, $WCl_6$, $WBr_5$, $WI_2$, or $C_9H_{12}W(CO)_3$ and any tungsten chloro-, bromo- or iodo-carbonyl compound.

Preferably, the iridium- and promoter-containing compounds are free of impurities which provide or generate in situ ionic iodides which may inhibit the reaction, for example, alkali or alkaline earth metal or other metal salts.

Ionic contaminants such as, for example, (a) corrosion metals, particularly nickel, iron and chromium and (b) phosphines or nitrogen containing compounds or ligands which may quaternise in situ; should be kept to a minimum in the liquid reaction composition as these will have an adverse effect on the reaction by generating $I^-$ in the liquid reaction composition which has an adverse effect on the reaction rate. Some corrosion metal contaminants such as for example molybdenum have been found to be less susceptible to the generation of $I^-$. Corrosion metals which have an adverse affect on the reaction rate may be minimised by using suitable corrosion-resistant materials of construction. Similarly, contaminants such as alkali metal iodides, for example lithium iodide, should be kept to a minimum. Corrosion metal and other ionic impurities may be reduced by the use of a suitable ion exchange resin bed to treat the reaction composition, or preferably a catalyst recycle stream. Such a process is described in U.S. Pat. No. 4,007,130. Preferably, ionic contaminants are kept below a concentration at which they would generate 500 ppm by weight of $I^-$, preferably less than 250 ppm by weight of in the liquid reaction composition.

Preferably, the concentration of methyl iodide in the liquid reaction composition is in the range 1 to 20 wt %, preferably 5 to 16 wt %.

The partial pressure of CO in the carbonylation reactor is suitably in the range 0.1 to 7 MPa preferably 0.1 to 3.5 MPa and most preferably 0.1 to 1.5 MPa.

The presence of $H_2$ in the CO feed and generated in situ by the water-gas shift reaction is preferably kept low as its presence may result in the formation of hydrogenation products. Thus, the molar ratio of $H_2$ to CO reactant is preferably less than 0.01:1, more preferably less than 0.005:1 and yet more preferably less than 0.003:1 and/or the partial pressure of $H_2$ in the carbonylation reactor is preferably less than 0.1 MPa, more preferably less than 0.05 MPa and yet more preferably less than 0.03 MPa.

The catalyst system used in the carbonylation process of the present invention has been found to be particularly beneficial at relatively low partial pressures of CO where the rate of reaction may be dependent upon the CO partial pressure. Under these conditions, it has been found that the catalyst system has the advantage of providing an increased rate of reaction over catalyst systems without the promoters of the present invention. This advantage allows for an increased rate of reaction under conditions when the CO partial pressure is relatively low, for example due to a low total pressure in the carbonylation reactor or due to high vapour pressure of components of the liquid reaction composition, e.g. at high methyl ethanoate concentration in the liquid reaction composition or due to a high concentration of inert gases (for example nitrogen and $CO_2$) in the carbonylation reactor. The catalyst system may also have advantages of increasing rate of carbonylation when the rate of reaction is reduced by the availability of CO in solution in the liquid reaction composition resulting from mass transfer limitations, for example due to poor agitation.

The pressure of the carbonylation reaction is suitably in the range 0.9 to 19.9 MPa, preferably 0.9 to 9.9 MPa, most preferably 1.4 to 4.9 MPa. The temperature of the carbonylation reaction is suitably in the range 100 to 300° C., preferably in the range 150 to 220° C.

Ethanoic acid may advantageously be used as a solvent for said carbonylation reaction.

The carbonylation process of the present invention may be performed as a batch or continuous process, preferably as a continuous process and may be performed in any suitable reactor, known to those skilled in the art.

The ethanoic acid product may be removed from the reactor by withdrawing liquid reaction composition and separating the ethanoic acid product by one or more flash and/or fractional distillation stages from the other components of the liquid reaction composition such as iridium catalyst, ruthenium and/or osmium and/or indium promoter, methyl iodide, water and unconsumed reactants which may be recycled to the reactor to maintain their concentrations in the liquid reaction composition. The ethanoic acid product may also be removed as a vapour from the stream exiting the carbonylation reactor.

Although halide promoters and stabilizers, such as methyl iodide, improve the efficiency and productivity of carbonylation processes, the continued presence of halide compounds in the carbonylation reaction products is undesirable if the product is employed as a starting material in a subsequent process employing a halide-sensitive catalyst where poisoning effects may be cumulative and irreversible. In a preferred embodiment the ethanoic acid product is purified of halide compounds. This purification treatment can be achieved by any appropriate method known to those skilled in the art. For example halides can be removed from the liquid phase using silver salts either unsupported, or supported, on an ion-exchange resin or a zeolite as exemplified in U.S. Pat. No. 5,344,976 and references therein.

According to the present invention, an ethanoic acid stream is introduced into an esterification unit, together with an alcohol(s) stream, in order to produce a stream comprising methyl ethanoate and/or ethyl ethanoate.

According to a preferred embodiment of the present invention, at least a part, preferably all, of the said ethanoic acid feed stream originates from the aforementioned carbonylation reaction; however in practice, it may also originate from another suitable source, such as wood pyrolysis and/or as a by-product of a fermentation process to produce alcohol(s).

The alcohol(s) stream comprises methanol and/or ethanol wherein, preferably at least a part of the methanol is produced during the aforementioned methanol synthesis stage, but may also originate from another appropriate source, such as a bio-fermentation process and/or wood pyrolysis. Similarly, the ethanol can also come from the aforementioned methanol synthesis stage as a by-product.

According to a preferred embodiment of the present invention, the molar ratio of alcohol(s) to ethanoic acid, introduced into the esterification reactor is 1; however molar ratios between 1.1 and 3; preferably between 1.1 and 2 may advantageously be used, as explained hereinafter.

The esterification reactor is preferably any reactor that is suitable for conducting an esterification reaction, for example using a close-coupled reactor and distillation column due to the reaction being equilibrium limited. The esterification reaction may also be conducted in a reactive distillation column.

The esterification of ethanoic acid by alcohol is a reaction which is known to be catalysed by strong inorganic acids such as hydrochloric or sulphuric acid. Such reactions have been described in many textbooks of organic chemistry, for example in chapter 10 of I. L. Finar, Organic Chemistry Vol I, Longmans, 1963.

The esterification of ethanoic acid together with alcohol(s) may be catalysed by any suitable acid catalysts (homogeneous and/or heterogeneous catalysts).

Examples of common commercial homogeneous catalysts include sulphonic acids, such as p-toluene sulphonic acid and alkyl sulphonic acids; where alkyl sulphonic acids may be represented by the formula $RSO_3H$ wherein R is a $C_1$ to $C_{12}$ substituted or unsubstituted aliphatic hydrocarbyl group and with the added proviso that the alkyl sulphonic acid has a de-sulphonation temperature in excess of 186° C. A preferred member of this class of sulphonic acids is methane sulphonic acid ($CH_3SO_3H$), as exemplified in EP 0158499, which has a de-sulphonation temperature in excess of 220° C.

However any sulphonic acid which has a de-sulphonation temperature greater or equal to that of p-toluene sulphonic acid is preferred as a catalyst. The de-sulphonation temperature of a sulphonic acid is defined as "the minimum temperature at which the reaction (de-sulphonation) occurs at a practical rate at atmospheric pressure" (see page 429 of E. E. Gilbert, Sulphonation and Related Reactions, Interscience, 1965). The de-sulphonation temperature of p-toluene sulphonic acid is 186° C. hence the sulphonic acids used in the present invention preferably have de-sulphonation temperatures in excess of this and preferably in excess of 190° C.

The sulphonic acid catalyst is added to the reaction mixture so as to comprise from 0.1 to 5 wt % of the reactor contents.

Alternatively, said esterification can also be catalysed by using tin-based catalysts, such as di-butyl tin oxide.

Heterogeneous esterification catalysts may be operated in the gas phase (e.g. acidic zeolites or heteropolyacids) or alternatively in the liquid phase (e.g. ion-exchange resins).

The esterification process described may be operated at atmospheric pressure but it is preferably operated at superatmospheric pressure between 0.11 and 0.8 MPa.

The temperature of esterification is preferably, greater than 80° C. and more preferably is in the range of 125 to 185° C.

The process may be operated continuously or batchwise. A suitable method for carrying out the esterification continuously is described in EP 0009886.

The reaction mixture may also contain in addition to the catalyst between 0.1 and 1 wt % of a corrosion inhibitor to reduce corrosion of the vessel. A preferred corrosion inhibitor is copper as a salt for example copper ethanoate.

According to the present invention the stream exiting the esterification reactor comprises methyl and/or ethyl ethanoate, as well as unreacted ethanoic acid, ethanol and/or methanol, esterification catalyst and water. This stream may be continuously removed from the reactor by distillation whilst the reaction occurs. According to a preferred embodiment of the present invention, the stream exiting the esterification reactor is purified to remove said ethanoic acid and esterification catalyst, before its introduction into the hydrogenation unit. After purification and before introduction into the hydrogenation unit, the ethanoate stream contains preferably less than 5 ppm wt of esterification catalyst, more preferably less than 1 ppm wt, most preferably less than 0.1 ppm wt. After purification and before introduction into the hydrogenation unit, the ethanoate stream contains preferably less than 5 wt % of ethanoic acid, more preferably less than 1 wt %, even more preferably less than 0.1 wt % and most preferably less than 100 ppm wt.

The applicants have unexpectedly found a preferred mode of operation whereby a methyl ethanoate/methanol mixture and/or an ethyl ethanoate/ethanol mixture can also advantageously be used together with the ethanoate as a feed to the hydrogenation unit; this is particularly advantageous because it considerably simplifies the purification process.

Furthermore the applicants have unexpectedly found that they can advantageously operate with certain amounts of water in the ethanoate or ethanoate and alcohol feed to the hydrogenation unit and that there is no need to use rigorous and expensive water separation processes such as those described in WO 8303409 on the feed obtained from the esterification unit. This is particularly advantageous because it further simplifies the hydrogenation feed purification process.

Thus, according to the present invention, methyl and/or ethyl ethanoate are introduced into a hydrogenation unit together with $H_2$, water and optionally, either or both, methanol or ethanol, to produce a stream comprising ethanol and optionally methanol. In addition to the product ethanol the outlet stream from the hydrogenation unit also comprises other reaction products (e.g. trace amounts of methane, ethane, diethyl ether, water and ethanal) and unreacted starting materials (e.g. methyl and/or ethyl ethanoate and $H_2$).

According to a preferred embodiment of the present invention, water represents between 0.5 and 20 mol %, preferably between 0.5 and 15 mol % and most preferably between 1 and 5 mol % of the total liquid feed (ethanoate, alcohol and water) to the hydrogenation reactor.

In fact, the applicants have unexpectedly and advantageously found that, by introducing a level of water (i.e. within the above specified range) into the hydrogenation reactor together with $H_2$ and the ethanoate stream, it is possible to increase the activity of the hydrogenation catalyst, which in turn increases the productivity towards ethanol. This is a clear advantage when compared to similar processes for producing ethanol, e.g. WO 8303409.

When methyl ethanoate is used as a feed for the hydrogenation process, it also produces ethyl ethanoate by transesterification. The proportion of ethyl ethanoate present in the exit stream will be determined by the nature of the catalyst and the degree of conversion. The proportion of ethyl ethanoate may be further increased, if desired, by introducing an acidic function into the catalyst to promote in situ transesterification. Preferably the hydrogenation unit is operated at high conversion of methyl and/or ethyl ethanoate to ethanol (and optionally methanol), such as more than 75%, preferably more than 90% and most preferably more than 95%.

It is has also been found to be an advantage of this process, that the selectivity of the methyl and/or ethyl ethanoate hydrogenation to ethanol can be further increased at the expense of undesirable by-products, such as the aforementioned alkanes (e.g. ethane and methane).

According to a preferred embodiment of the present invention, at least a part, preferably all of the said methyl and/or ethyl ethanoate stream emanates from the aforementioned esterification reactor.

As mentioned hereinabove, the applicants have unexpectedly found an additional advantage whereby a methyl ethanoate/methanol mixture and/or an ethyl ethanoate/ethanol mixture from the esterification reactor is used as the feed for the hydrogenation unit. Said advantage being that the applicants were able to retain a high selectivity towards the production of ethanol, whilst using the aforementioned feed, as well as providing a method for reducing the exotherm of the hydrogenation reaction, thus increasing the lifetime of the hydrogenation catalyst. This is particularly advantageous when using an adiabatic mode of operation for the hydrogenation reaction.

Preferably, at least a part, preferably all, of the $H_2$ fed into the hydrogenation unit emanates from the synthesis gas generation procedure (i.e. it is obtained during the aforementioned $CO/H_2$ separation), where, if need be, the $H_2$ content can be further increased by subjecting the said synthesis gas to a water-gas shift reaction and a subsequent $H_2$ separation.

In fact the applicants have unexpectedly found that when operating the present invention, by using the aforementioned cryogenic separation to separate the synthesis gas, or a method that results in a similar degree of separation, it is advantageous to obtain and use substantially pure $H_2$ to feed the hydrogenation reactor. This is because it has been found that by introducing pure $H_2$ into the hydrogenation reactor, the applicants were able to operate a much more integrated and improved synthesis gas management system, as it meant that the total pressure of the hydrogenation reactor could be substantially lower, when compared to introducing an $H_2$ feed that contained a large amount of diluent (e.g. synthesis gas), and consequently much less gas was needed to operate the hydrogenation reactor in a effective manner.

According to the present invention, substantially pure hydrogen refers to a $H_2$ feed that contains less than 10 mol %, preferably less than 5 mol % and most preferably less than 2 mol % of CO.

Alternatively the $H_2$ stream may originate from a variety of other chemical processes, including ethene crackers, styrene manufacture and catalytic reforming. However, it is known that the main commercial processes for purposeful generation of $H_2$ are autothermal reforming, steam reforming and partial oxidation of hydrocarbonaceous feedstocks such as natural gas, coal, coke, deasphalter bottoms, refinery residues and biomass. $H_2$ may also be produced by electrolysis of water.

The overall choice of technology for producing $H_2$ is generally determined by the following economic considerations and factors:
  i. feedstock cost
  ii. feedstock availability
  iii. capital cost
  iv. local energy and operating costs; and
  v. environmental considerations The catalyst(s) employed in the hydrogenation unit is selected from any of the following:
  (i) a precious metal based catalyst, comprising of at least one noble metal from Group. VIII of the periodic table (CAS version, for example iron, ruthenium, osmium, cobalt, rhodium, iridium, nickel, palladium, platinum) and at least one of the metals chosen from rhenium, tungsten and/or molybdenum; and optionally an additional metal, that is capable of alloying with said Group VIII noble metal; or
  (ii) a copper-based catalyst (for example a copper chromite or a mixed copper metal oxide-based catalyst wherein the second metal can be copper, zinc, zirconium or manganese).

According to a preferred embodiment of the present invention, the catalyst(s) employed in the hydrogenation unit is a copper-based catalyst, more preferably comprising copper and zinc, most preferably consisting of copper-zinc-oxide.

All of the aforementioned catalysts may advantageously be supported on any suitable support known to those skilled in the art; non-limiting examples of such supports include carbon, silica, titania, clays, aluminas, zinc oxide, zirconia and mixed oxides. Preferably, the palladium-based catalyst is supported on carbon. Preferably, the copper-based catalyst is supported on zinc oxide and preferably comprises between 20 and 40 wt % of copper.

According to a preferred embodiment of the present invention, the catalyst(s) employed is heterogeneous.

The hydrogenation process may be operated in a gas phase, or a mixed gas/liquid phase regime. The mixed gas/liquid phase regime is where the reactant mixture, at the reactor conditions, is below the dew point temperature.

The hydrogenation can be conducted in batch or semi continuous or continuous mode. Continuous mode of operation is the most preferred.

The hydrogenation reaction can be conducted in adiabatic or isothermal mode; where adiabatic mode of operation is preferred. Suitable reactors include single, or a plurality, of adiabatic bed reactors which can be used in series or parallel. For reactors utilised in series, heat exchangers and/or intercoolers and/or additional reactant and/or recycle of intermediates can be employed in between successive reactors to control the reaction temperature. The preferred adiabatic temperature rise is less than 50° C., preferably less than 25° C. and most preferably less than 10° C. The preferred use of adiabatic reactors is in series. The adiabatic reactors may be operated at different temperatures depending on composition of the individual reactor feeds.

The hydrogenation can also be conducted in multi-tubular reactors in which case a cooling/heating medium is circulated around the tubes to control the temperature. For exothermic reactions, as such, there will be a radial temperature gradient in the reactor, the preferred gradient is less than 50° C. preferably less than 25° C. most preferably less than 10° C. The preferred flow regime in this type of reactor is turbulent rather than laminar, this corresponds to a Reynolds number greater than 2100 (where the velocity is approximated by velocity in an unpacked tube).

The hydrogenation reaction can also be conducted in other reactor types such as fluidised bed, spinning basket and buss loop, heat exchanger reactors. A mixed liquid/gas phase hydrogenation reaction can be conducted with co-flow or counterflow of the $H_2$ and gas to the liquid (e.g. a bubble reactor). The preferred mode of operation of gas/liquid reactors is co-flow, also known as trickle bed operation; this can be conducted in at least one tubular and/or multi-tubular reactor in series. The hydrogenation reaction may change from a mixed gas/liquid phase to a fully gas phase reaction, as the reaction proceeds down the reactor. The mixed phase hydrogenation can also be conducted in other types of reactors, or within a combination of different reactors, for example in a slurry or stirred tank reactor with, or without, external circulation and optionally operated as a cascade or stirred tanks, a loop reactor or a Sulzer mixer-reactor.

The hydrogenation reactor(s) preferably operate at a temperature of more than 150° C., but less than 290° C.

According to a preferred embodiment of the present invention the reaction temperature is more than 150° C., preferably more than 170° C. and most preferably more than 190° C.; and less than 250° C.

The hydrogenation reaction may be operated at a pressure of more than 3 MPa, preferably at a pressure of more than 5 MPa; and at a pressure of less than 15 MPa, more preferably at a pressure less than 13 MPa and most preferably at a pressure less than 9 MPa.

According to an embodiment of the present invention, when the hydrogenation unit(s) is operated with a copper-based catalyst, the feed mixture introduced into the reactor(s) is always above its dew point temperature.

The GHSV for continuous operation may be in the range 50 to 50,000 $h^{-1}$, preferably from 1,000 to 30,000 $h^{-1}$ and most preferably from 2,000 to 9,000 $h^{-1}$.

The ester liquid substrate introduced into the hydrogenation unit preferably has an LHSV less than 10 $h^1$, more preferably less than 5 $h^{-1}$ and most preferably less than 3 $h^1$; for example, a typical LHSV for normal operation is approximately 1 $h^{-1}$.

According to the present invention, the stream exiting the hydrogenation unit is then subjected to a separation stage (e.g. distillation), whereby a fraction comprising alcohol(s) (i.e. methanol and/or ethanol) is separated and recovered and at least a part of the recovered alcohol(s) is used as the alcohol(s) feed for the esterification unit. When the ester feed to the hydrogenation unit consists of methyl ethanoate then the methanol produced during hydrogenation is separated and preferably recycled to the esterification unit. Likewise, when the ester feed to the hydrogenation unit consists of ethyl ethanoate then part of the ethanol, preferably more than 40% and less than 51%, produced during hydrogenation is separated and preferably recycled to the esterification unit and the remaining ethanol is recovered as the desired product.

During the separation stage an unreacted fraction comprising methyl and/or ethyl ethanoate and/or $H_2$ may also be preferably recovered and recycled back into said esterification unit.

Additionally, another separation embodiment at the exit of the hydrogenation unit consists of isolating a methyl ethanoate/methanol mixture and/or an ethyl ethanoate/ethanol mixture and recycling said isolated compounds to the esterification unit. Preferably and advantageously the said methyl ethanoate/methanol mixture, and/or the said ethyl ethanoate/ethanol mixture, additionally contains water.

According to a preferred embodiment of the present invention, the molar ratio of $H_2$ to [methyl ethanoate and ethyl ethanoate] that is introduced into the hydrogenation unit is greater than 2:1, preferably the molar ratio is greater than 4:1 and most preferably the molar ratio is greater than 5:1; and is less than 100:1, preferably less than 50:1 and most preferably less than 15:1.

It should be noted that whilst all of the aforementioned temperature and pressure operating conditions form preferred embodiments of the present invention, they are not, by any means, intended to be limiting, and the present invention hereby includes any other pressure and temperature operating conditions that achieve the same effect.

FIG. 2, is a simplified flow diagram for one embodiment of the present invention and an improved process for the production of ethanol from carbonaceous feedstock is shown. A carbonaceous feed stream is supplied to the synthesis gas generation unit, 201, through line 221 and a stream comprising water and/or oxygen is supplied to the synthesis gas generation unit through line 222. Synthesis gas from the synthesis gas generation unit is passed to a synthesis gas separation zone, 202, through line 223. In the synthesis gas separation zone crude synthesis gas from the synthesis gas generation zone is separated to provide synthesis gas as well as CO and $H_2$ streams. Water is removed from the synthesis gas separation unit through line 240. Synthesis gas from the synthesis gas separation zone is fed to the methanol synthesis zone, 203, through line 224. In the methanol synthesis zone synthesis gas is converted to methanol in a methanol synthesis reactor and methanol is separated from the methanol synthesis reactor product stream. A purge stream is taken from the methanol synthesis zone through line 242 to control the build up of diluent in the methanol synthesis zone. Methanol is fed from the methanol synthesis zone to the carbonylation reactor, 204, through line 227. CO from the synthesis gas separation zone is fed to the carbonylation reactor through line 225. Methanol and CO are reacted together in the carbonylation reactor in a liquid reaction composition which comprises ethanoic acid, an iridium catalyst, methyl iodide, water and at least one promoter. A purge stream is taken from the carbonylation reactor through line 241 to control the build up of diluent gases in the carbonylation reactor. The liquid reaction composition from the carbonylation reactor is passed to an ethanoic acid separation and purification zone, 205, through line 228. Ethanoic acid is separated from the carbonylation reaction liquid reaction composition in the ethanoic acid separation and purification zone. A stream comprising the iridium catalyst, methyl iodide, water and promoter is returned to the carbonylation reactor from the ethanoic acid separation and purification zone through line 239. Ethanoic acid is further purified of halide compounds in the ethanoic acid separation and purification zone. Ethanoic acid is fed from the ethanoic acid separation and purification zone to the esterification and ester separation zone, 206, through line 229. A stream comprising ethanol and ethyl ethanoate is fed to the esterification and separation zone through line 234. Ethanoic acid and ethanol are converted, in the presence of a catalyst, in the esterification and separation zone to ethyl ethanoate and water. Ethyl ethanoate is separated in the esterification and separation zone from the catalyst, which is retained in the esterification and separation zone. Most of the water is separated in the esterification and separation zone and is removed from the process through line 231. A stream comprising ethyl ethanoate and water and optionally comprising ethanol is passed to the hydrogenation reactor, 207, through line 230. $H_2$ from the synthesis gas separation zone is fed to the hydrogenation reactor through the line 226. The hydrogenation reactor contains a solid hydrogenation catalyst and the reactor is maintained at conditions of temperature and pressure so that a gas phase reaction takes place. A stream comprising ethanol, $H_2$, ethyl ethanoate and water is passed from the hydrogenation reactor to the alcohol separation zone, 208, through line 232. A gas stream comprising $H_2$ is separated in the alcohol separation zone and passed back to the hydrogenation reactor as a gas recycle stream through line 235. A purge stream is taken from the gas recycle stream through line 236 to control the build up of diluent gases in the hydrogenation reactor. A stream comprising ethanol and ethyl ethanoate is recycled from the ethanol separation zone to the esterification and ester separation zone through line 234. Water is removed from the process from the alcohol separation zone through line 238. A product ethanol stream is taken from the process from the ethanol separation zone through line 233.

FIG. 3, is a simplified flow diagram of another embodiment of the present invention and an improved process for the production of ethanol from carbonaceous feedstock is shown. A carbonaceous feed stream is supplied to the synthesis gas generation unit, 301, through line 321 and a stream comprising water and/or oxygen is supplied to the synthesis gas generation unit through line 322. Synthesis gas from the synthesis gas generation unit is passed to a synthesis gas separation zone, 302, through line 323. In the synthesis gas separation zone crude synthesis gas from the synthesis gas generation zone is separated to provide synthesis gas as well as CO and $H_2$ streams. Water is removed from the synthesis gas separation unit through line 340. Synthesis gas from the synthesis gas separation zone is fed to the methanol synthesis zone, 303, through line 324. In the methanol synthesis zone synthesis gas is converted to methanol in a methanol synthesis reactor and methanol is separated from the methanol synthesis reactor product stream. A purge stream is taken from the methanol synthesis zone through line 342 to control the build up of diluent in the methanol synthesis zone. Methanol is fed from the methanol synthesis zone to the carbonylation reactor, 304, through line 327. CO from the synthesis gas separation zone is fed to the carbonylation reactor through line 325. Methanol and CO are reacted together in the carbonylation reactor in a liquid reaction composition which comprises ethanoic acid, an iridium catalyst, methyl iodide, water and at least one promoter. A purge stream is taken from the carbonylation reactor through line 341 to control the build up of diluent gases in the carbonylation reactor. The liquid reaction composition from the carbonylation reactor is passed to an ethanoic acid separation and purification zone, 305, through line 328. Ethanoic acid is separated from the carbonylation reaction liquid reaction composition in the ethanoic acid separation and purification zone. A stream comprising the iridium catalyst, methyl iodide, water and promoter is returned to the carbonylation reactor from the ethanoic acid separation and purification zone through line 339. Ethanoic acid is further purified of halide compounds in the ethanoic acid separation and purification zone. Ethanoic acid is fed from the ethanoic acid separation and purification zone to the esterification and ester separation zone, 306, through line 329. A stream comprising methanol, methyl ethanoate and ethyl ethanoate is fed to the esterification and separation zone through line 334. Ethanoic acid and methanol are converted, in the presence of a catalyst, in the esterification and separation zone to methyl ethanoate and water. Methyl ethanoate is separated in the esterification and separation zone from the catalyst, which is retained in the esterification and separation zone. Water is separated in the esterification and separation zone and is removed from the process through line 331. A stream comprising methyl ethanoate, water and optionally comprising methanol is passed to the hydrogenation reactor, 307, through line 330. $H_2$ from the synthesis gas separation zone is fed to the hydrogenation reactor through the line 326. The hydrogenation reactor contains a solid hydrogenation catalyst and the reactor is maintained at conditions of temperature and pressure so that a gas phase reaction takes place. A stream comprising methanol, ethanol, $H_2$, methyl ethanoate, ethyl ethanoate and water is passed from the hydrogenation reactor to the alcohol separation zone, 308, through line 332. A gas stream comprising $H_2$ is separated in the alcohol separation zone and passed back to the hydrogenation reactor as a gas recycle stream through line 335. A purge stream is taken from the gas recycle stream through line 336 to control the build up of diluent gases in the hydrogenation reactor. A stream comprising methanol, methyl ethanoate and ethyl ethyl ethanoate is recycled from the ethanol separation zone to the esterification and ester separation zone through line 334. Water is removed from the process from the alcohol separation zone through line 338. A product ethanol stream is taken from the process from the ethanol separation zone through line 333.

EXAMPLES

Examples 1-5 demonstrates the promotional effect of water on the hydrogenolysis of methyl ethanoate and ethyl ethanoate using a copper-based catalyst.

Catalysts

The catalyst used in these Examples was Pricat CZ 2912T (supplied by Johnson Matthey), which has the following composition: CuO (35 wt %), ZnO (65 wt %).

Catalyst Testing

The catalyst testing experiments were carried out in a pressure flow reactor. The catalyst was heated to 100° C. under a flow of 5 mol % $H_2$ in $N_2$ at 2.5 MPa and a GHSV of 6000 $h^{-1}$. The concentration of $H_2$ was increased in stages to 10, 20, 40, 70 and 100 mol % with a 1 h dwell time at each stage. The catalyst was heated at 1° C./min to a holding temperature of 180° C. and was held for a dwell time of 24 h. At this point catalyst activation was considered complete.

Example 1

A mixture of $H_2$ (90.9 vol %), methyl ethanoate (8.65 vol %) and water (0.45 vol %) was passed over Pricat CZ 29/2T at 200° C., with a pressure of 5 MPa and a GHSV of 4500 $h^{-1}$ for 18 h. The concentration of water in the ester feed was 5 mol %. The observed productivity, conversion and selectivity results for Example 1 are given in Table 1. Productivity is defined as kilograms of ethanol plus kilograms of the ethyl portion of ethyl ethanoate produced per kilogram of catalyst per hour (kg/kg$_{cat}$/h). Selectivity is defined as selectivity to ethanol and the ethyl portion of ethyl ethanoate.

Example 2

A mixture of $H_2$ (90.9 vol %), methyl ethanoate (8.87 vol %) and water (0.23 vol %) was passed over Pricat CZ 29/2T at 200° C., with a pressure of 5 MPa and a GHSV of 4500 $h^{-1}$ for 20 hours. The concentration of water in the ester feed was 2.5 mol %. The observed productivity, conversion and selectivity results for Example 2 are given in Table 1. Productivity is defined as kilograms of ethanol plus kilograms of the ethyl portion of ethyl ethanoate produced per kilogram of catalyst per hour (kg/kg$_{cat}$/h). Selectivity is defined as selectivity to ethanol and the ethyl portion of ethyl ethanoate.

Example 3

Comparative Example

A mixture of $H_2$ (90.9 vol %) and methyl ethanoate (9.1 vol %) was passed over Pricat CZ 29/2T at 200° C., with a pressure of 5 MPa and a GHSV of 4500 $h^{-1}$ for 20 h. The observed productivity, conversion and selectivity results for Example 3 are given in Table 1. Productivity is defined as kilograms of ethanol plus kilograms of the ethyl portion of ethyl ethanoate produced per kilogram of catalyst per hour (kg/kg$_{cat}$/h). Selectivity is defined as selectivity to ethanol and the ethyl portion of ethyl ethanoate.

TABLE 1

Results for Examples 1-3.

| Example | Water concentration in ester feed (mol %) | Productivity kg/kg$_{cat}$/h | Conversion (%) | Selectivity (%) |
|---|---|---|---|---|
| 1 | 5 | 0.46 | 87.1 | 100 |
| 2 | 2.5 | 0.53 | 97.3 | 99.9 |
| 3 | 0 | 0.41 | 70.5 | 99.9 |

Example 4

A mixture of $H_2$ (90.45 vol %), ethyl ethanoate (8.65 vol %) and water (0.90 vol %) was passed over Pricat CZ 29/2T at 200° C., with a pressure of 5 MPa and a GHSV of 4500 $h^{-1}$ for 20 h. The concentration of water in the ester feed was 9.4 mol %. The observed productivity, conversion and selectivity results for Example 4 are given in Table 2. Productivity is defined as kilograms of ethanol produced per kilogram of catalyst per hour (kg/kg$_{cat}$/h). Selectivity is defined as selectivity to ethanol.

Example 5

Comparative Example

A mixture of $H_2$ (90.9 vol %) and ethyl ethanoate (9.1 vol %) was passed over Pricat CZ 29/2T at 200° C., with a pressure of 5 MPa and a GHSV of 4500 for 20 h. The observed productivity, conversion and selectivity results for Example 5 are given in Table 2. Productivity is defined as kilograms of ethanol produced per kilogram of catalyst per hour (kg/kg$_{cat}$/h). Selectivity is defined as selectivity to ethanol.

TABLE 2

Results for Examples 4 and 5.

| Example | Water concentration in ester feed (mol. %) | Productivity kg/kg$_{cat}$/h | Conversion (%) | Selectivity (%) |
|---|---|---|---|---|
| 4 | 9.4 | 0.49 | 91.7 | 100 |
| 5 | 0 | 0.48 | 82.9 | 99.9 |

The invention claimed is:

1. A process for the production of ethanol from ethanoic acid and H$_2$, characterised by the following steps:
   1) introducing ethanoic acid, together with methanol and/or ethanol into an esterification reactor containing an esterification catalyst to produce methyl ethanoate and/or ethyl ethanoate,
   2) introducing methyl ethanoate and/or ethyl ethanoate from step 1, together with H$_2$ and water, into a hydrogenation unit comprising a hydrogenation catalyst to produce a stream comprising ethanol, unreacted methyl ethanoate and/or ethyl ethanoate and optionally methanol,
   3) separating the resulting stream, from step 2, into unreacted methyl ethanoate and/or ethyl ethanoate and ethanol and optionally methanol,
   4) optionally reintroducing methyl ethanoate and/or ethyl ethanoate, from step 3, into the esterification reactor of step 1,
   5) using at least a part of the methanol and/or the ethanol of step 3, as the methanol and/or ethanol feed of the esterification reactor of step 1, and
   6) recovering ethanol, from step 3.

2. A process according to claim 1, wherein the molar ratio of the [methanol and ethanol] to ethanoic acid, introduced into the esterification reactor is between 1.1 and 3.

3. A process according to claim 1, wherein the methyl ethanoate and/or ethyl ethanoate stream exiting the esterification reactor, which also contains unreacted ethanoic acid and residual esterification catalyst, is subjected to a purification step to remove said ethanoic acid and esterification catalyst before introduction into the hydrogenation unit.

4. A process according to claim 1, wherein water represents between 0.5 and 20 mol % of the total liquid feed (methyl ethanoate and/or ethyl ethanoate, alcohol and water) entering the hydrogenation unit.

5. A process according to claim 4, wherein water represents between 0.5 and 15 mol % of the total liquid feed (methyl ethanoate and/or ethyl ethanoate, alcohol and water) entering the hydrogenation unit.

6. A process according to claim 1, wherein the catalyst(s) employed in the hydrogenation unit is a copper-based catalyst.

7. A process according to claim 1, wherein the catalyst(s) employed in the hydrogenation unit comprises copper and zinc.

8. A process according to claim 1, wherein the molar ratio of H$_2$ to [methyl ethanoate and ethyl ethanoate] that is introduced into the hydrogenation unit, is greater than 2:1; and is less than 100:1.

9. A process according to claim 1, wherein a methyl ethanoate/methanol mixture is recovered from the stream exiting the hydrogenation unit and is recycled into the esterification reactor.

10. A process according to claim 1, wherein an ethyl ethanoate/ethanol mixture is recovered from the stream exiting the hydrogenation unit and is recycled into the esterification reactor.

* * * * *